United States Patent
Goto et al.

(10) Patent No.: US 12,275,699 B2
(45) Date of Patent: Apr. 15, 2025

(54) EICOSAPENTAENOIC ACID ALKYL ESTER-CONTAINING COMPOSITION AND METHOD FOR PRODUCING SAME

(71) Applicant: NISSHIN PHARMA INC., Chiyoda-ku (JP)

(72) Inventors: Ichiro Goto, Ueda (JP); Masataka Harata, Ueda (JP); Shingo Nonaka, Ueda (JP)

(73) Assignee: NISSHIN PHARMA INC., Chiyoda-ku (JP)

( * ) Notice: Subject to any disclaimer, the term of this patent is extended or adjusted under 35 U.S.C. 154(b) by 889 days.

(21) Appl. No.: 17/418,439

(22) PCT Filed: Dec. 26, 2019

(86) PCT No.: PCT/JP2019/051107
§ 371 (c)(1),
(2) Date: Jun. 25, 2021

(87) PCT Pub. No.: WO2020/138282
PCT Pub. Date: Jul. 2, 2020

(65) Prior Publication Data
US 2021/0395183 A1 Dec. 23, 2021

(30) Foreign Application Priority Data
Dec. 26, 2018 (JP) .................. 2018-242417

(51) Int. Cl.
*C07C 69/587* (2006.01)
*C07C 67/54* (2006.01)

(52) U.S. Cl.
CPC ............ *C07C 69/587* (2013.01); *C07C 67/54* (2013.01)

(58) Field of Classification Search
CPC .............................. C07C 69/587; C07C 67/54
See application file for complete search history.

(56) References Cited

U.S. PATENT DOCUMENTS

| | | | |
|---|---|---|---|
| 5,990,164 A | 11/1999 | Horrobin et al. | |
| 9,365,800 B2* | 6/2016 | Harata | C07C 67/54 |
| 10,597,607 B2* | 3/2020 | Harata | C07C 67/48 |
| 10,899,994 B2* | 1/2021 | Ikemoto | C07C 69/587 |
| 11,767,491 B2* | 9/2023 | Ikemoto | C11C 1/02 |
| | | | 554/175 |
| 2015/0126760 A1 | 5/2015 | Doisaki et al. | |
| 2015/0247106 A1 | 9/2015 | Sondbe et al. | |
| 2015/0252288 A1 | 9/2015 | Harata et al. | |
| 2017/0252315 A1 | 9/2017 | Doisaki et al. | |

FOREIGN PATENT DOCUMENTS

| CN | 106795452 A | 5/2017 |
|---|---|---|
| JP | 2015-105354 A | 6/2015 |
| JP | 2016-502573 A | 1/2016 |
| TW | 514633 B | 12/2002 |
| WO | WO 2013/172346 A1 | 11/2013 |
| WO | WO 2014/054435 A1 | 4/2014 |
| WO | WO 2016/043251 A1 | 3/2016 |

OTHER PUBLICATIONS

Abe et al. (1984), Concentration of Ethyl Icosapentaenoate From Japanese Sardine Oil by Molecular Sieve Column†. Fette, Seifen, Anstrichm., 86: 8-10. (Year: 1984).*
Combined Chinese Office Action and Search Report issued Feb. 27, 2023, in Chinese Patent Application No. 201980086203.8 (with English translation), 23 pages.
Registry (online), Columbus, OH, USA, 59157-37-8, Nov. 16, 1998, 1 page.
International Search Report issued Mar. 31, 2020 in PCT/JP2019/051107 filed Dec. 26, 2019, 3 pages.
Fardin-Kia, A., et al., "Separation of the Fatty Acids in Menhaden Oil as Methyl Esters with a Highly Polar Ionic Liquid Gas Chromatographic Column and Identification by Time of Flight Mass spectrometry", Lipids, vol. 48, No. 12, 2013, pp. 1279-1295.
Sippola, E., et al., "Temperature Program Optimization by Computer Simulation for the Capillary GC Analysis of Fatty Acid Methyl Esters on Biscyanopropyl Siloxane Phases", Journal of High Resolution Chromatography, vol. 16, No. 2, 1993, pp. 95-100.
Extended European Search Report issued Sep. 6, 2022 in European Patent Application No. 19902643.6, 10 pages.
Sandri et al., "Syntheses of all-(Z)-5,8,11,14,17-Eicosapentaenoic Acid and all-(Z)-4,7,10,13,16,19-Docosahexaenoic Acid from (Z)-1,1,6,6-Tetraisopropoxy-3-hexene", J. Org. Chem, vol. 60, No. 20, 1995, pp. 6627-6630, XP055955102.
Pubchem, "(4Z,7Z,10Z,13Z,16Z)-4,7,10,13,16,19-Icosahexaenoic acid methyl ester", Pubchem 101639173, 2015, pp. 1-8, XP055955100, Retrieved from the Internet: URL:https://pubchemc.ncbi.nlm.nih.gov/compound/101639173.
Wikipedia Contributors: "Chromatography detector", Wikipedia, The Free Encyclopedia, 2018, pp. 1-2, XP055955286, Retrieved from the Internet: URL:https://en.wikipedia.org/w/index.php?title=Chromatography_detector&oldid=861602252.

* cited by examiner

*Primary Examiner* — Matthew P Coughlin
*Assistant Examiner* — Ashli Ariana Chicks
(74) *Attorney, Agent, or Firm* — Oblon, McClelland, Maier & Neustadt, L.L.P.

(57) ABSTRACT

Provided is a high-concentration and high-purity eicosapentaenoic acid-containing composition. A method for producing an eicosapentaenoic acid alkyl ester-containing composition, the method includes: (1) bringing a raw oil that contains an eicosapentaenoic acid alkyl ester into contact with an aqueous solution that contains a silver salt, and then collecting an aqueous layer; (2) adding an organic solvent to the aqueous layer, and then collecting an organic solvent layer; and (3) subjecting the organic solvent layer to vacuum distillation at a temperature of 180 to 188° C. and a tower top vacuum degree of 0.7 Pa or below, to recover the eicosapentaenoic acid alkyl ester from the organic solvent layer.

6 Claims, No Drawings

EICOSAPENTAENOIC ACID ALKYL ESTER-CONTAINING COMPOSITION AND METHOD FOR PRODUCING SAME

CROSS-REFERENCE TO RELATED APPLICATIONS

This application is a National Stage of International Application No. PCT/JP2019/051107, filed Dec. 26, 2019, and claims priority to Japanese Application No. 2018-242417, filed Dec. 26, 2018.

TECHNICAL FIELD

The present invention relates to an eicosapentaenoic acid alkyl ester-containing composition and a method for producing the same.

BACKGROUND ART

Polyunsaturated fatty acid (PUFA) such as eicosapentaenoic acid (EPA) and docosahexaenoic acid (DHA) has recently been clarified regarding their pharmacological effects, and has been used as raw materials for pharmaceuticals and health foods. PUFA is however not easily obtainable by chemical synthesis, due to a plurality of double bonds contained therein. Most of industrially used PUFA is produced by extracting or refining PUFA-rich biological oil-and-fat materials, such as fish oil.

The biological oil-and-fat materials are, however, mixtures of a large variety of fatty acids which are different in the number of carbon atoms, and number and position of double bonds contained therein, and compositional ratios of stereoisomers, so that content of PUFA is not always large. Further, PUFA refined from a biological oil-and-fat material contains various trace impurities derived from the oil-and-fat per se, or produced by heat treatment during the refining process. Such impurities may include, for example, fatty acids that are unfavorable for cardiovascular events such as arachidonic acid, saturated fatty acids, and trans isomers of PUFA; and environmental pollutants that are hazardous to living body such as environmental hormone. Therefore, the PUFA-containing composition, as a raw material for pharmaceuticals and health foods, has been desired not only to be PUFA-rich, but also to have possibly lowest content of the impurities that may adversely affect the living body.

Methods for producing high-purity PUFA-containing compositions have been disclosed so far. Patent Literature 1 discloses a method for producing a PUFA ethyl ester with reduced content of environmental pollutant, the method includes removing, by thin film distillation, environmental pollutant such as polychlorinated dibenzoparadioxin (PCDD) and polychlorinated dibenzofuran (PCDF), from a raw oil that contains PUFA as a constituent fatty acid. Patent Literature 2 describes a method for producing a high-concentration EPA alkyl ester-containing composition with contents of arachidonic acid ester and monotrans isomer of EPA alkyl ester suppressed at certain levels or below, the method includes subjecting an EPA alkyl ester-containing composition to precision distillation at 0.2 Torr at 190° C. or lower, followed by chromatographic condensation. Patent Literature 3 describes a method for removing unfavorable components in an oil composition, such as hydrophilic component including proteinaceous compound, or lipophilic components including environmental pollutants and cholesterol, by treating the oil composition with an aqueous fluid, and then typically stripped by short-path distillation. Patent Literature 4 describes a method for producing refined fish oil, the method includes bringing fish oil into contact with alkali and then with activated clay, and then bringing the fish oil at 150 to 230° C. into contact with steam typically by vacuum steam distillation for deodorization. Patent Literature 5 describes production of a PUFA alkyl ester-containing composition with an extremely low content of trans isomer, as a result of bringing a polyunsaturated fatty acid alkyl ester into contact with an aqueous solution containing a silver salt, followed by vacuum distillation at 170 to 190° C., and a tower top vacuum degree of 1 Pa or below.

CITATION LIST

Patent Literature

Patent Literature 1: WO 2013/172346 A1
Patent Literature 2: WO 2016/043251 A1
Patent Literature 3: JP 2016-502573 A
Patent Literature 4: JP 2015-105354 A
Patent Literature 5: WO 2014/054435 A1

SUMMARY OF INVENTION

Technical Problem

The present inventors found that the EPA-containing compositions produced by conventional methods (the method described in Patent Literature 5, for example) contain unnoticed impurities, and that the impurities are novel EPA analogs having not been known before. Since the impurities were unnoticed substances, so far, EPA has not been refined paying special attention to such impurities. Further, it is extremely difficult to remove the impurities from the EPA-containing composition, due to a close similarity between chemical structures of the impurities and that of EPA. For these reasons, the impurities are supposed to have been contained in the conventional EPA-containing compositions without being noticed. Removal of these impurities can further improve purity of the EPA-containing composition.

The present invention is therefore to provide a high-concentration, high-purity EPA-containing composition free of the aforementioned unnoticed EPA analogs, and a method for producing the same.

Solution to Problem

According to the present invention, there is provided a method for producing an eicosapentaenoic acid alkyl ester-containing composition, the method includes:

(1) bringing a raw oil containing an eicosapentaenoic acid alkyl ester into contact with an aqueous solution containing a silver salt, and then collecting an aqueous layer;

(2) adding an organic solvent to the aqueous layer, and then collecting an organic solvent layer; and (3) subjecting the organic solvent layer to vacuum distillation at a temperature of 180 to 188° C. and a tower top vacuum degree of 0.7 Pa or below, to recover the eicosapentaenoic acid alkyl ester from the organic solvent layer.

According to the present invention, there is also provided an eicosapentaenoic acid alkyl ester-containing composition that contains 95 area % or more of an eicosapentaenoic acid alkyl ester, and 0.1 area % or less of each of (4Z,7Z,10Z,13Z,16Z)-icosa-4,7,10,13,16-pentaenoic acid alkyl ester, (7Z,10Z,13Z,16Z,19Z)-icosa-7,10,13,16,19-pentaenoic acid alkyl ester, and (4Z,7Z,10Z,13Z,16Z,19Z)-icosa-4,7,10,13, 16,19-hexaenoic acid alkyl ester.

According to the present invention, there is also provided a method for measuring purity of an eicosapentaenoic acid alkyl ester-containing composition, the method includes measuring content, in the composition, of at least one substance selected from the group consisting of (4Z,7Z,10Z, 13Z,16Z)-icosa-4,7,10,13,16-pentaenoic acid alkyl ester, (7Z,10Z,13Z,16Z,19Z)-icosa-7,10,13,16,19-pentaenoic acid alkyl ester, and (4Z,7Z,10Z,13Z,16Z,19Z)-icosa-4,7,10,13, 16,19-hexaenoic acid alkyl ester.

According to the present invention there is also provided (4Z,7Z,10Z,13Z,16Z)-icosa-4,7,10,13,16-pentaenoic acid alkyl ester, (7Z,10Z,13Z,16Z,19Z)-icosa-7,10,13,16,19-pentaenoic acid alkyl ester, or (4Z,7Z,10Z,13Z,16Z,19Z)-icosa-4,7,10,13,16,19-hexaenoic acid alkyl ester.

Advantageous Effects of Invention

A high-concentration, high-purity EPA-containing composition having contents as low as possible of fatty acids that may adversely affect the living body is useful as a raw material for pharmaceuticals and health foods. According to the present invention, there is provided an EPA-containing composition with higher concentration and higher purity, with reduced contents not only of arachidonic acid, having been removed before as an impurity, but also of EPA analogs having not been recognized as the impurities.

DESCRIPTION OF EMBODIMENTS

The present invention relates to unnoticed impurities having been contained in the conventional eicosapentaenoic acid (EPA) alkyl ester-containing composition.

A high-concentration, high-purity eicosapentaenoic acid (EPA)-containing composition having contents as low as possible of impurities such as fatty acid and trans isomers, which may adversely affect the living body, is useful as a raw material for pharmaceuticals and health foods. In search of the EPA-containing composition with higher purity, the present inventors detected and identified the impurities contained in the conventional EPA-containing compositions. The present inventors consequently found that the EPA alkyl ester-containing compositions obtainable by the conventional methods (the method described in Patent Literature 5, for example) contain the impurities below, having never been noticed before:

(4Z,7Z,10Z,13Z,16Z)-icosa-4,7,10,13,16-pentaenoic acid alkyl ester;

(7Z,10Z,13Z,16Z,19Z)-icosa-7,10,13,16,19-pentaenoic acid alkyl ester; and (4Z,7Z,10Z,13Z,16Z,19Z)-icosa-4,7,10,13,16,19-hexaenoic acid alkyl ester.

All of these three substances are EPA analogs, and were found to be novel substances having never been noticed. In the patent specification, these three substances are also collectively referred to as impurities of the present invention, hereinafter. The impurities of the present invention can be those separated from the EPA alkyl ester-containing composition. It is extremely difficult to isolate the impurities of the present invention from EPA by the conventional methods for purifying EPA, due to a close similarity between chemical structures of the impurities and that of EPA, and this is supposedly the reason why the impurities of the present invention have been neither separated nor identified so far.

In search of producing the EPA-containing composition with still higher purity, the present inventors went through extensive studies into a method for removing the impurities of the present invention from the EPA alkyl ester-containing composition, and developed an improved method for producing the EPA alkyl ester-containing composition.

One aspect of the present invention therefore relates to a method for producing an EPA alkyl ester-containing composition with reduced contents of the impurities of the present invention. Another aspect of the present invention relates to an EPA alkyl ester-containing composition with reduced contents of the impurities of the present invention, which is produced by the production method.

In the production method of the present invention, the raw oil of the EPA alkyl ester-containing composition can be prepared from biological oils and fats containing EPA. Examples of the biological oils and fats include those derived from marine animals such as fish and plankton, and those derived from microorganisms such as algae, and among them, preferred examples include oils and fats derived from fish such as sardines, mackerel and tuna, and oils and fats derived from algae. These biological oils and fats mainly contain fatty acids in the form of triglycerides in which three fatty acid molecules are bound to one glycerin molecule. Also diglycerides, monoglycerides and free fatty acids may be contained although in small amounts.

The biological oils and fats are preferably those containing 20 area % or more of EPA, with respect to the total fatty acids contained therein. EPA may be present in the biological oils and fats in the form of free fatty acid, or may be present in the form of fatty acid chain of mono-, di- or triglyceride. Ratio of each constituent fatty acid in the total fatty acids in oils and fats can be measured by gas chromatography under the conditions described later.

The biological oils and fats are prepared as raw oils in the production method of the present invention, by converting the contained EPA into an alkyl ester, optionally followed by concentration of EPA. The EPA alkyl ester can be produced, for example, by subjecting an EPA-containing oil and fat and an acid having a desired alkyl group, to an esterification reaction according to a known method. Alternatively, an EPA alkyl ester can be obtained by allowing EPA in the glyceride contained in the biological oil and fat, to react with a lower alcohol in the presence of a catalyst or an enzyme, to cause alkyl esterification. The higher the degree of alkyl esterification, the more suitable, wherein preferably 90% or more, and more preferably 95% or more of the total amount of the target PUFA (including the free form) contained in the raw oil is alkyl esterified. Alkyl group that composes the EPA alkyl ester is exemplified by straight-chain or branched alkyl group having 1 to 6 carbon atoms, which is preferably methyl group or ethyl group, and is more preferably ethyl group.

The oils and fats that contain the EPA alkyl ester, used as the raw oil, may be commercially available oils and fats. From the viewpoint of obtaining high content of the EPA alkyl ester, preferably used is commercially available fish oil-derived oil and fat whose content of EPA is standardized. The raw oil used in the production method of the present invention is preferably any of oils and fats that contains 40 area % or more of EPA with respect to the total fatty acids contained therein. According to the production method of the present invention, the composition with high concentration of EPA is finally obtainable, by using a raw oil with an EPA content of 40 area % or more, with respect to the total fatty acids.

In each step of the method for producing an EPA alkyl ester-containing composition of the present invention, the above-mentioned raw oil is preferably applied in the form of liquid. The raw oil, if being in the form of liquid at the reaction temperature of each step, can be directly applied to each step of the present invention. The raw oil, if being in the form of solid at the reaction temperature of each step, can be applied after being properly dissolved in or diluted with an organic solvent or other oil. The organic solvent usable here is the one separable from water in view of enabling the step (1) below, and is exemplified by ethyl acetate, chloroform, carbon tetrachloride, diethyl ether and hexane.

The method for producing an EPA alkyl ester-containing composition of the present invention includes:

(1) bringing a raw oil that contains an EPA alkyl ester into contact with an aqueous solution that contains a silver salt, and then collecting an aqueous layer;

(2) adding an organic solvent to the aqueous layer, and then collecting an organic solvent layer; and (3) subjecting the organic solvent layer to vacuum distillation at a temperature of 180 to 188° C. and a tower top vacuum degree of 0.7 Pa or below, to recover the EPA alkyl ester from the organic solvent layer.

The steps (1) and (2) in the production method of the present invention are steps of isolating and purifying the EPA alkyl ester from the raw oil, by utilizing changes in solubility of the EPA-containing polyunsaturated fatty acid (PUFA) alkyl ester in the extraction solvent, caused by formation of a complex between the silver salt and the carbon-carbon double bond of PUFA. More specifically, the step (1) is a step of bringing the raw oil that contains the EPA alkyl ester into contact with the aqueous solution that contains the silver salt, and then collecting the aqueous layer. The step can be carried out according to the methods described in, for example, Japanese Patent No. 2786748, Japanese Patent No. 2895258, Japanese Patent No. 2935555, and Japanese Patent No. 3001954.

More specifically, the aqueous solution that contains the silver salt is added to the above-mentioned raw oil that contains the EPA alkyl ester, and the mixture is stirred for 5 minutes to 4 hours, preferably about 10 minutes to 2 hours. The reaction temperature at this time is preferably determined, while setting the upper limit so as to allow the product of the step (1) to exist completely in the liquid form, which is typically about 80° C. or lower, meanwhile the lower limit is typically 5° C. or higher. The reaction temperature is more preferably around room temperature (20 to 30° C.). The reaction produces a silver-EPA complex. Since the complex dissolves in the aqueous solution layer, EPA can be selectively recovered by collecting the aqueous layer from the solution.

The silver salt is not particularly limited so long as it can form a complex with the unsaturated bond of PUFA, to which silver nitrate, silver perchlorate, silver tetrafluoroborate, silver acetate and so forth are applicable. Of these, silver nitrate is preferred. The solvent for the aqueous solution is exemplified by water, or a mixed medium of water with a hydroxy group-containing compound such as glycerin or ethylene glycol, wherein water is preferred. Silver salt concentration in the aqueous solution may only be 0.1 mol/L or higher, and is preferably about 1 to 20 mol/L. Molar ratio of PUFA and silver salt is about 1:100 to 100:1, preferably about 1:5 to 1:1.

The step (2) in the production method of the present invention is a step of adding the organic solvent to the aqueous layer collected in the step (1), so as to extract the EPA alkyl ester in the aqueous layer into the organic solvent layer, and then collecting the organic solvent layer that contains the EPA alkyl ester. The step can be carried out according to the methods described for example in Japanese Patent No. 2786748, Japanese Patent 2895258, Japanese Patent 2935555, and Japanese Patent 3001954.

The organic solvent to be added to the aqueous layer, capable of highly solubilizing PUFA and is separable from water, is exemplified by hexane, ether, ethyl acetate, butyl acetate, chloroform, cyclohexane, benzene, toluene and xylene. The solution (reaction solution) having the organic solvent added thereto is preferably heated up to a temperature higher than the reaction temperature in the step (1), that is, the temperature at which the silver-EPA complex produces. The temperature is more preferably set higher by 20° C. or more than the reaction temperature in the step (1), that is, the temperature at which the complex produces. In an exemplary case where the complex is allowed to produce at room temperature in the step (1), the temperature of the reaction solution in the step (2) is preferably 40° C. or higher, and more preferably about 50 to 80° C. Time for extraction reaction of the EPA alkyl ester into the organic solvent layer may be 10 minutes to 6 hours, and preferably 30 minutes to 2 hours, wherein the solution is preferably stirred during the reaction. The aqueous layer is then removed, to thereby collect the organic solvent layer that contains the EPA alkyl ester. The collected organic solvent layer may alternatively be allowed to pass through an adsorbent such as silica gel, activated carbon or silicon dioxide, so as to further remove residual silver ion.

In one embodiment, the steps (1) and (2) may alternatively be carried out according to a method described in WO 2017/191821, instead of mixing the raw oil with the aqueous solution, or mixing the aqueous solution with the organic solvent in batch. That is, droplets of the silver salt-containing aqueous solution are allowed to pass through the EPA alkyl ester-containing raw oil filled in a first reaction tank, so as to bring the aqueous solution into contact with the raw oil, to thereby produce the aqueous solution that contains the silver-EPA complex, and the aqueous solution is then collected. Droplets of the thus collected aqueous solution that contains the silver-EPA complex are then allowed to pass through an organic solvent filled in a second reaction tank, so as to extract the EPA alkyl ester into the organic solvent, and the organic solvent layer that contains the EPA alkyl ester is collected. Passage of the droplets of the aqueous solution through the raw oil and collection of the aqueous solution that contains the silver-EPA complex; and/or, passage of the droplets of the aqueous solution that contains the silver-EPA complex through the organic solvent and collection of the organic solvent layer that contains the EPA alkyl ester; may be preferably conducted concurrently, and preferably continuously, while as needed, adding the aqueous solution, and optionally adding the raw oil or the organic solvent, into the first and/or second reaction tanks. Although passage time of the aqueous solution in the first and second reaction tanks (time of contact with the raw oil or with the organic solvent) can be controlled depending on difference of specific gravity between the aqueous solution and the raw oil or the organic solvent, and depending on volume of the raw oil or the organic solvent (size of the reaction tanks), the passage time can alternatively be controlled by controlling flow rate and flow volume of the aqueous solution, and optionally flow rate and flow volume of the raw oil or the organic solvent, in the reaction tanks with use of, for example, a pump. Temperatures of the liquids in the first and second reaction tanks may be same as the aforementioned temperatures of the reaction liquids in the steps (1) and (2), respectively. The present embodiment further enables recycling of the silver salt-containing aqueous solution remained after contact with the organic solvent, for use in the next contact with the raw oil. The present embodiment can therefore reduce consumption of the silver salt-containing aqueous solution down to about ½ to 1/20, as compared with the method of adding all of the silver salt-containing aqueous solution to the aforementioned raw oil, followed by stirring.

The step (3) of the production method of the present invention is a step of subjecting the organic solvent layer obtained in the step (2) to vacuum distillation, to recover the target EPA alkyl ester. More specifically, the target EPA alkyl ester is selectively recovered from the organic solvent layer that contains the EPA alkyl ester obtained in the step (2), on the basis of difference of boiling points.

For the vacuum distillation in the step (3), applicable is any of known types of vacuum distillation apparatus, including those of packed column type, spring type, or tray type, which may be based on a continuous distillation system. On the other hand, the vacuum distillation in the method of the present invention is conditioned at lower pressure and narrower temperature range, as compared with those in the conventional method of vacuum distillation (the method described in Patent Literature 5, for example). That is, in the method of the present invention, the conditions for vacuum distillation in step (3) include a tower top vacuum degree of distiller of 0.7 Pa or below, and a distillation temperature of 180 to 188° C., and preferably of 185 to 188° C. The tower top vacuum degree, if exceeding 0.7 Pa, will degrade separation from the impurities of the present invention, making it difficult to recover the high-purity EPA alkyl ester. In addition, the distillation temperature, if falls below 180° C., will elongate the distillation time required for concentrating EPA or for removing the impurities of the present invention, meanwhile if exceeds 188° C., will not properly improve the distillation efficiency as may be expected from increase of energy cost, and the process will cost high. The distillation temperature in this step is given by temperature of the organic solvent layer that contains the EPA alkyl ester.

A fraction that contains the EPA alkyl ester obtained in the vacuum distillation step may be refluxed, and subjected again to vacuum distillation under the foregoing conditions.

In the method for producing the EPA alkyl ester-containing composition of the present invention, the individual steps are carried out in the order of (1)→(2)→(3). Any change made in this order will fail in obtaining the composition having a high content of the target EPA and a sufficiently low proportion of the impurities of the present invention. In particular, the step (3) preceding to the step (1) or (2) will make it difficult to obtain the composition having a high content of the target EPA, or will give the composition having a high content of EPA, but also high contents of the impurities of the present invention.

The EPA alkyl ester-containing composition produced by the production method of the present invention preferably contains 95 area % or more of EPA alkyl ester in the total fatty acids contained therein, which is more preferably 96 area % or more, even more preferably 98 area % or more, and yet more preferably 99 area % or more.

In the present specification, content of a certain fatty acid in the oil-and-fat composition is represented by percentage (area %) of peak area of such fatty acid to the total peak area of all fatty acids in the composition, when measured by gas chromatography under the following conditions.

Sample

Nine microliters of measurement sample, diluted into 1.5 mL of n-hexane

Column Conditions

Column: A capillary column composed of a fused silica tube of column inside diameter of 0.25 mm and column length of 60 m, coated with polyethylene glycol to a film thickness of 0.25 μm
(e.g. DB-WAX, from J&W, Inc.)
Column temperature: 210° C.
He flow rate: 1.3 mL/min Detection Conditions $H_2$ flow rate: 30 mL/min, air flow rate: 400 mL/min
DET temperature: 260° C.
The column conditions and detection conditions may alternatively be as follows.

Column Conditions

Column: A non-chemical bond type capillary column composed of a fused silica tube of column inside diameter of 0.25 mm and column length of 100 m, coated with cyanopropyl to a film thickness of 0.20 μm (for example, TC-2560, 0.25 mm×100 m×0.20 μm, from GL Sciences, Inc.)
Column temperature: 170° C. (150 min hold)→heating (10° C./min)
→240° C. (15 min hold)
He flow rate: 1.0 to 1.5 mL/min Detection Conditions $H_2$ flow rate: 30 mL/min, air flow rate: 400 mL/min
DET temperature: 270° C.
Content of the impurities of the present invention in the EPA alkyl ester-containing composition is 0.1 area % or less, for each of (4Z,7Z,10Z,13Z,16Z)-icosa-4,7,10,13,16-pentaenoic acid alkyl ester, (7Z,10Z,13Z,16Z,19Z)-icosa-7,10, 13,16,19-pentaenoic acid alkyl ester, and (4Z,7Z,10Z,13Z, 16Z,19Z)-icosa-4,7,10,13,16,19-hexaenoic acid alkyl ester. Preferably, in the EPA alkyl ester-containing composition, content of (4Z,7Z,10Z,13Z,16Z)-icosa-4,7,10,13,16-pentaenoic acid alkyl ester is 0.1 area % or less, content of (7Z,10Z,13Z,16Z,19Z)-icosa-7,10,13,16,19-pentaenoic acid alkyl ester is 0.07 area % or less, and content of (4Z,7Z, 10Z,13Z,16Z,19Z)-icosa-4,7,10,13,16,19-hexaenoic acid alkyl ester is 0.09 area % or less. More preferably, in the EPA alkyl ester-containing composition, the content of (4Z, 7Z,10Z,13Z,16Z)-icosa-4,7,10,13,16-pentaenoic acid alkyl ester is 0.05 area % or less, the content of (7Z,10Z,13Z, 16Z,19Z)-icosa-7,10,13,16,19-pentaenoic acid alkyl ester is 0.07 area % or less, and the content of (4Z,7Z,10Z,13Z,16Z, 19Z)-icosa-4,7,10,13,16,19-hexaenoic acid alkyl ester is 0.08 area % or less.

In a preferred embodiment, the EPA alkyl ester-containing composition has an EPA alkyl ester content of 95 area % or more, preferably 96 area % or more, more preferably 98 area % or more, still more preferably 99 area % or more, and, has a content of each of (4Z,7Z,10Z,13Z,16Z)-icosa-4,7,10,13, 16-pentaenoic acid alkyl ester, (7Z,10Z,13Z,16Z,19Z)-icosa-7,10,13,16,19-pentaenoic acid alkyl ester, and (4Z,7Z, 10Z,13Z,16Z,19Z)-icosa-4,7,10,13,16,19-hexaenoic acid alkyl ester of 0.1 area % or less.

In a more preferred embodiment, the EPA alkyl ester-containing composition has an EPA alkyl ester content of 95 area % or more, preferably 96 area % or more, more preferably 98 area % or more, and still more preferably 99 area % or more; a content of (4Z,7Z,10Z,13Z,16Z)-icosa-4,7,10,13,16-pentaenoic acid alkyl ester of 0.1 area % or less; a content of (7Z,10Z,13Z,16Z,19Z)-icosa-7,10,13,16,19-pentaenoic acid alkyl ester of 0.07 area % or less; and a content of (4Z,7Z,10Z,13Z,16Z,19Z)-icosa-4,7,10,13,16,19-hexaenoic acid alkyl ester of 0.09 area % or less.

In a more preferred embodiment, the EPA alkyl ester-containing composition has an EPA alkyl ester content of 98 area % or more, and preferably 99 area % or more; a content of (4Z,7Z,10Z,13Z,16Z)-icosa-4,7,10,13,16-pentaenoic acid alkyl ester of 0.05 area % or less; a content of (7Z,10Z,13Z,16Z,19Z)-icosa-7,10,13,16,19-pentaenoic acid alkyl ester of 0.07 area % or less; and a content of (4Z,7Z,10Z,13Z,16Z,19Z)-icosa-4,7,10,13,16,19-hexaenoic acid alkyl ester of 0.08 area % or less.

The present inventors further found that the contents of the impurities of the present invention, since being EPA analogs which are hardly separable from EPA, can serve as an index of the purity of the EPA alkyl ester-containing composition. A further aspect of the present invention therefore relates to a method of measuring the purity of the EPA alkyl ester-containing composition, which includes measuring the contents of the impurities of the present invention.

More specifically, in the method for measuring the purity of the EPA alkyl ester-containing composition according to the present invention, measured is at least one substance selected from the group consisting of (4Z,7Z,10Z,13Z,16Z)-icosa-4,7,10,13,16-pentaenoic acid alkyl ester, (7Z,10Z,13Z,16Z,19Z)-icosa-7,10,13,16,19-pentaenoic acid alkyl ester, and (4Z,7Z,10Z,13Z,16Z,19Z)-icosa-4,7,10,13,16,19-hexaenoic acid alkyl ester. Content of the substance can be calculated, for example, from a percentage of a peak area of such substance to the total peak area of all fatty acids, measured by gas chromatography under the foregoing conditions. Content of the measured substance in the EPA alkyl ester-containing composition indicates the level of contamination of the measured substance with respect to the target EPA, and represents purity of the target EPA in the composition, considering that the impurities of the present invention are hardly separable from EPA.

In a preferred embodiment, the EPA alkyl ester-containing composition is judged to be highly pure, if the content of any of (4Z,7Z,10Z,13Z,16Z)-icosa-4,7,10,13,16-pentaenoic acid alkyl ester, (7Z,10Z,13Z,16Z,19Z)-icosa-7,10,13,16,19-pentaenoic acid alkyl ester, or (4Z,7Z,10Z,13Z,16Z,19Z)-icosa-4,7,10,13,16,19-hexaenoic acid alkyl ester in the EPA alkyl ester-containing composition is 0.5 area % or less, preferably 0.3 area % or less, and more preferably 0.1 area % or less. More specifically, the EPA alkyl ester-containing composition is judged to be sufficiently pure as a raw material for pharmaceuticals or foods.

In a more preferred embodiment, the EPA alkyl ester-containing composition is judged to be highly pure, if the contents of all of (4Z,7Z,10Z,13Z,16Z)-icosa-4,7,10,13,16-pentaenoic acid alkyl ester, (7Z,10Z,13Z,16Z,19Z)-icosa-7,10,13,16,19-pentaenoic acid alkyl ester, and (4Z,7Z,10Z,13Z,16Z,19Z)-icosa-4,7,10,13,16,19-hexaenoic acid alkyl ester in the EPA alkyl ester-containing composition are 0.5 area % or less, preferably 0.3 area % or less, and more preferably 0.1 area % or less. More specifically, the EPA alkyl ester-containing composition is judged to be sufficiently pure as a raw material for pharmaceuticals or foods.

In a more preferred embodiment, the EPA alkyl ester-containing composition is judged to be highly pure, if the content, in the EPA alkyl ester-containing composition, of (4Z,7Z,10Z,13Z,16Z)-icosa-4,7,10,13,16-pentaenoic acid alkyl ester is 0.1 area % or less, the content of (7Z,10Z,13Z,16Z,19Z)-icosa-7,10,13,16,19-pentaenoic acid alkyl ester is 0.07 area % or less, and the content of (4Z,7Z,10Z,13Z,16Z,19Z)-icosa-4,7,10,13,16,19-hexaenoic acid alkyl ester is 0.09 area % or less. More specifically, the EPA alkyl ester-containing composition is judged to be sufficiently pure as a raw material for pharmaceuticals or foods.

In a more preferred embodiment, the EPA alkyl ester-containing composition is judged to be highly pure, if the content, in the EPA alkyl ester-containing composition, of (4Z,7Z,10Z,13Z,16Z)-icosa-4,7,10,13,16-pentaenoic acid alkyl ester is 0.05 area % or less, the content of (7Z,10Z,13Z,16Z,19Z)-icosa-7,10,13,16,19-pentaenoic acid alkyl ester is 0.07 area % or less, and the content of (4Z,7Z,10Z,13Z,16Z,19Z)-icosa-4,7,10,13,16,19-hexaenoic acid alkyl ester is 0.08 area % or less. More specifically, the EPA alkyl ester-containing composition is judged to be sufficiently pure as a raw material for pharmaceuticals or foods.

The method for measuring the purity of the EPA alkyl ester-containing composition according to the present invention may further measure the content of the EPA alkyl ester in the EPA alkyl ester-containing composition.

Therefore, in a more preferred embodiment, the EPA alkyl ester-containing composition is judged to be highly pure, if the content of the EPA alkyl ester in the EPA alkyl ester-containing composition is 95 area % or more, preferably 96 area % or more, even more preferably 98 area % or more, and yet more preferably 99 area %; and if the contents of all of (4Z,7Z,10Z,13Z,16Z)-icosa-4,7,10,13,16-pentaenoic acid alkyl ester, (7Z,10Z,13Z,16Z,19Z)-icosa-7,10,13,16,19-pentaenoic acid alkyl ester, and (4Z,7Z,10Z,13Z,16Z,19Z)-icosa-4,7,10,13,16,19-hexaenoic acid alkyl ester are 0.5 area % or less, preferably 0.3 area % or less, and more preferably 0.1 area % or less. More specifically, the EPA alkyl ester-containing composition is judged to be sufficiently pure as a raw material for pharmaceuticals or foods.

In a more preferred embodiment, the EPA alkyl ester-containing composition is judged to be highly pure, if the content of the EPA alkyl ester in the EPA alkyl ester-containing composition is 95 area % or more, preferably 96 area % or more, even more preferably 98 area % or more, and yet more preferably 99 area % or more; and if the content of (4Z,7Z,10Z,13Z,16Z)-icosa-4,7,10,13,16-pentaenoic acid alkyl ester is 0.1 area % or less, the content of (7Z,10Z,13Z,16Z,19Z)-icosa-7,10,13,16,19-pentaenoic acid alkyl ester is 0.07 area % or less, and the content of (4Z,7Z,10Z,13Z,16Z,19Z)-icosa-4,7,10,13,16,19-hexaenoic acid alkyl ester is 0.09 area % or less. More specifically, the EPA alkyl ester-containing composition is judged to be sufficiently pure as a raw material for pharmaceuticals or foods.

In a more preferred embodiment, the EPA alkyl ester-containing composition is judged to be highly pure, if the content of the EPA alkyl ester in the EPA alkyl ester-containing composition is 98 area % or more, and more preferably 99 area % or more; and if the content of (4Z,7Z,10Z,13Z,16Z)-icosa-4,7,10,13,16-pentaenoic acid alkyl ester is 0.05 area % or less, the content of (7Z,10Z,13Z,16Z,19Z)-icosa-7,10,13,16,19-pentaenoic acid alkyl ester is 0.07 area % or less, and the content of (4Z,7Z,10Z,13Z,16Z,19Z)-icosa-4,7,10,13,16,19-hexaenoic acid alkyl ester is 0.08 area % or less. More specifically, the EPA alkyl ester-containing composition is judged to be sufficiently pure as a raw material for pharmaceuticals or foods.

EXAMPLES

Hereinafter, the present invention will be described in more detail with reference to examples, to which the present invention is not limited.

Reference Example 1: Compositional Analysis of Fatty Acids

Nine microliters of a measurement sample was diluted into 1.5 mL of n-hexane, and fatty acids were analyzed under the following conditions using a gas chromatographic analyzer (Type 6890 GC; from Agilent Technologies, Inc.). Content of the fatty acid were calculated as the percentage (area %) of the peak area of each fatty acid to the total peak area of all fatty acids on a chromatogram.

Column Conditions

Column: DB-WAX, from J&W, Inc., 0.25 mm×60 m
(Capillary column composed of a fused silica tube of column inside diameter of 0.25 mm and column length of 60 m, coated with polyethylene glycol to a film thick ness of 0.25 μm)
Column temperature: 210° C.
He flow rate: 1.3 mL/min Detection Conditions $H_2$ flow rate: 30 mL/min, air flow rate: 400 mL/min
DET temperature: 260° C.
or, Column Conditions Column: TC-2560, 0.25 mm×100 m×0.20 μm, from GL Sciences, Inc.
(Non-chemical bond type capillary column composed of a fused silica tube of column inside diameter of 0.25 mm and column length of 100 m, coated with cyanopropyl to a film thickness of 0.20 μm)
Column temperature: 170° C. (150 min hold)→heating (10° C./min)
→240° C. (15 min hold)
He flow rate: 1.0 to 1.5 mL/min Detection Conditions $H_2$ flow rate: 30 mL/min, air flow rate: 400 mL/min
DET temperature: 270° C.

Reference Example 2: Preparation of Raw Oil

To 2 kg of sardine oil, 2000 mL of dehydrated ethanol solution with 100 g of sodium hydroxide dissolved therein was added, the mixture was mixed and stirred at 70 to 80° C. for one hour, 1000 mL of water was then added and mixed thoroughly, and the mixture was allowed to stand still for one hour. A separated aqueous layer was removed, and an oil layer was washed several times with water until the washing solution became neutral, to thereby obtain ethyl esterified sardine oil. The fatty acid composition of the sardine oil was examined according to Reference Example 1. As summarized in Table 1, the sardine oil was found to contain, in the total fatty acids, 20.4 area % of EPA, 0.047 area % (0.0023 relative to EPA) of (4Z,7Z,10Z,13Z,16Z)-icosa-4,7,10,13,16-pentaenoic acid, 0.018 area % (0.0009 relative to EPA) of (7Z,10Z,13Z,16Z,19Z)-icosa-7,10,13,16,19-pentaenoic acid, and 0.024 area % (0.0012 relative to EPA) of (4Z,7Z,10Z,13Z,16Z,19Z)-icosa-4,7,10,13,16,19-hexaenoic acid.

One gram of the prepared ethyl esterified sardine oil was vacuum distilled at a tower top vacuum degree of 13.3 Pa and a distillation temperature of 120° C. to 170° C., to obtain a crude product. The fatty acid composition of the crude product was examined according to Reference Example 1. As summarized in Table 1, the crude product was found to contain, in the total fatty acids, 44.0 area % of EPA, 0.097 area % (0.0022 relative to EPA) of (4Z,7Z,10Z,13Z,16Z)-icosa-4,7,10,13,16-pentaenoic acid, 0.040 area % (0.0009 relative to EPA) of (7Z,10Z,13Z,16Z, 19Z)-icosa-7,10,13,16,19-pentaenoic acid, and 0.053 area % (0.0012 relative to EPA) of (4Z,7Z,10Z,13Z,16Z,19Z)-icosa-4,7,10,13,16,19-hexaenoic acid. The crude product was used as a raw oil in following Examples.

Example 1: Production of EPA-Containing Composition

Step (1): To 300 g of the raw oil obtained in Reference Example 2, 160 mL of n-hexane was added, and thoroughly mixed for dissolution. Five hundred milliliters of a 50 mass % aqueous silver nitrate solution was added thereto, and the mixture was then stirred under condition at 5 to 30° C. After allowing the mixed solution to stand still, the separated n-hexane layer was removed, and the aqueous layer was collected.

Step (2): To the thus collected aqueous layer, 2000 mL of n-hexane was newly added, and mixed thoroughly at 52 to 68° C., to thereby extract a fatty acid ethyl ester in the aqueous layer into n-hexane. After allowing the mixed solution to stand still, the separated aqueous layer was removed and the n-hexane layer was concentrated.

The fatty acid composition of the n-hexane layer obtained in Step (2) was examined according to Reference Example 1. As summarized in Table 1, the fatty acid ethyl ester contained in the n-hexane layer was found to contain, in the total fatty acids, 74.5 area % of EPA, as well as 0.156 area % (0.0021 relative to EPA) of (4Z,7Z,10Z,13Z,16Z)-icosa-4,7,10,13,16-pentaenoic acid, 0.067 Area % (0.0009 relative to EPA) of (7Z,10Z,13Z, 16Z,19Z)-icosa-7,10,13,16,19-pentaenoic acid, and 0.089 area % (0.0012 relative to EPA) of (4Z,7Z,10Z,13Z,16Z, 19Z)-icosa-4,7,10,13,16,19-hexaenoic acid.

Step (3): The n-hexane layer that contains the fatty acid ethyl ester obtained in Step (2) was subjected to vacuum distillation by using a packed column type precision distiller, while being kept conditioned at a tower top vacuum degree of 0.7 Pa or below, and a distillation temperature of 180 to 183° C., to thereby obtain an EPA ethyl ester-containing composition. The fatty acid composition of the thus obtained composition was examined according to Reference Example 1. As summarized in Table 1, the composition was found to contain, in the total fatty acids, 98.4 area % of EPA, as well as 0.098 area % (0.0010 relative to EPA) of (4Z,7Z,10Z,13Z,16Z)-icosa-4,7,10,13,16-pentaenoic acid, 0.069 area % (0.0007 to EPA) of (7Z,10Z,13Z,16Z,19Z)-icosa-7,10,13,16,19-pentaenoic acid, and 0.089 area % (0.0009 to EPA) of (4Z,7Z,10Z,13Z,16Z,19Z)-icosa-4,7,10,13,16,19-hexaenoic acid.

Example 2

An EPA ethyl ester-containing composition was obtained according to the same procedures as in Example 1, except that in Step (3) the tower top vacuum degree was set to 0.7 Pa, and the distillation temperature was set to 180° C. to 188° C. The fatty acid composition of the thus obtained composition was examined according to Reference Example 1. As summarized in Table 1, the composition was found to contain, in the total fatty acids, 98.2 area % of EPA, as well as 0.079 area % (0.0008 relative to EPA) of (4Z,7Z,10Z,13Z,16Z)-icosa-4,7,10,13,16-pentaenoic acid, 0.069 area % (0.0007 relative to EPA) of (7Z,10Z,13Z,16Z,19Z)-icosa-7,10,13,16,19-pentaenoic acid, and 0.088 area % (0.0009 relative to EPA) of (4Z,7Z,10Z,13Z,16Z,19Z)-icosa-4,7,10,13,16,19-hexaenoic acid.

Example 3

An EPA ethyl ester-containing composition was obtained according to the same procedures as in Example 1, except that in Step (3) the tower top vacuum degree was set to 0.7 Pa, and the distillation temperature was set to 185° C. to 188° C. The fatty acid composition of the thus obtained composition was examined according to Reference Example 1. As summarized in Table 1, the composition was found to contain, in the total fatty acids, 99.0 area % of EPA, as well as 0.050 area % (0.0005 relative to EPA) of (4Z,7Z,10Z,13Z,16Z)-icosa-4,7,10,13,16-pentaenoic acid, 0.069 area % (0.0007 relative to EPA) of (7Z,10Z,13Z,16Z,19Z)-icosa-7,10,13,16,19-pentaenoic acid, and 0.079 area % (0.0008 relative to EPA) of (4Z,7Z,10Z,13Z,16Z,19Z)-icosa-4,7,10,13,16,19-hexaenoic acid.

COMPARATIVE EXAMPLE 1

An EPA ethyl ester-containing composition was obtained according to the same procedures as in Example 1, except that in Step (3) the tower top vacuum degree was set to 0.9 to 1.0 Pa, and the distillation temperature was set to 172° C. to 188° C. The fatty acid composition of the thus obtained composition was examined according to Reference Example 1. As summarized in Table 1, the composition was found to have a high EPA content of 98.3 area %, but also found to have high contents of the impurities, that is, (4Z,7Z,10Z,13Z,16Z)-icosa-4,7,10,13,16-pentaenoic acid, (7Z,10Z,13Z,16Z,19Z)-icosa-7, 10, 13, 16, 19-pentaenoic acid, and (4Z,7Z,10Z,13Z,16Z,19Z)-icosa-4, 7,10, 13, 16, 19-hexaenoic acid, of 0.157 area % (0.0016 relative to EPA), 0.088 area % (0.0009 relative to EPA), and 0.108 area % (0.0011 relative to EPA), respectively, proving high contents of (4Z,7Z,10Z,13Z,16Z)-icosa-4,7,10,13,16-pentaenoic acid, and (4Z,7Z,10Z,13Z,16Z,19Z)-icosa-4,7, 10, 13, 16, 19-hexaenoic acid.

TABLE 1

| | Area % (ratio relative to EPA) | | | | | | |
|---|---|---|---|---|---|---|---|
| | Raw oil | Example 1 | | Example 2 | Example 3 | Comparative Example 1 |
| | Sardine oil | Before step (1) | After step (2) | After step (3) | After step (3) | After step (3) | After step (3) |
| Distillation Degree of vacuum (Pa) | | | | ~0.7 | ~0.7 | ~0.7 | 0.9~1.0 |
| Temperature (° C.) | | | | 180-183 | 180-188 | 185-188 | 172-188 |
| (5Z, 8Z, 11Z, 14Z, 17Z)-Icosa-5, 8, 11, 14, 17-pentaenoic acid (EPA) | 20.4 | 44.0 | 74.5 | 98.4 | 98.2 | 99.0 | 98.3 |
| (4Z, 7Z, 10Z, 13Z, 16Z)-Icosa-4, 7, 10, 13, 16-pentaenoic acid | 0.047 (0.0023) | 0.097 (0.0022) | 0.156 (0.0021) | 0.098 (0.0010) | 0.079 (0.0008) | 0.050 (0.0005) | 0.157 (0.0016) |
| (7Z, 10Z, 13Z, 16Z, 19Z)-Icosa-7, 10, 13, 16, 19-pentaenoic acid | 0.018 (0.0009) | 0.040 (0.0009) | 0.067 (0.0009) | 0.069 (0.0007) | 0.069 (0.0007) | 0.069 (0.0007) | 0.088 (0.0009) |
| (4Z, 7Z, 10Z, 13Z, 16Z, 19Z)-Icosa-4, 7, 10, 13, 16, 19-hexaenoic acid | 0.024 (0.0012) | 0.053 (0.0012) | 0.089 (0.0012) | 0.089 (0.0009) | 0.088 (0.0009) | 0.079 (0.0008) | 0.108 (0.0011) |

As summarized in Table 1, the ratios of the impurities relative to EPA, in Step (2) in Example 1, were found to be almost the same as those in the raw oil, proving that the impurities were concentrated together with EPA. In contrast, the impurities were found to decrease while the EPA was concentrated in Step (3) in Example 1, proving that the impurities were separated from the EPA in Step (3). In addition, the ratios of the impurities relative to EPA were found to be almost same between the raw oil and the product in Step (2) in Comparative Example 1, demonstrating importance of conditions of vacuum distillation in Step (3) for separation of the impurities.

The invention claimed is:

1. A method for producing an eicosapentaenoic acid alkyl ester-containing composition, the method comprising:
   bringing a raw oil that comprises an eicosapentaenoic acid alkyl ester into contact with an aqueous solution that comprises a silver salt;
   collecting an aqueous layer from the aqueous solution;
   adding an organic solvent to the aqueous layer;
   collecting an organic solvent layer from the organic solvent;
   subjecting the organic solvent layer to vacuum distillation at a temperature of from 185° C. to 188° C. and a tower top vacuum degree of 0.7 Pa or below; and
   recovering the eicosapentaenoic acid alkyl ester from the organic solvent layer to produce the eicosapentaenoic acid alkyl ester-containing composition.

2. The method according to claim 1, wherein the eicosapentaenoic acid alkyl ester-containing composition comprises at least 95 area % of eicosapentaenoic acid alkyl ester, and 0.1 area % or less of each of (4Z,7Z,10Z,13Z,16Z)-icosa-4,7,10,13,16-pentaenoic acid alkyl ester, (7Z,10Z,13Z,16Z,19Z)-icosa-7,10,13,16,19-pentaenoic acid alkyl ester, and (4Z,7Z,10Z,13Z,16Z,19Z)-icosa-4,7,10,13,16,19-hexaenoic acid alkyl ester.

3. The method according to claim 2, wherein the eicosapentaenoic acid alkyl ester-containing composition comprises 0.1 area % or less of (4Z,7Z,10Z,13Z,16Z)-icosa-4,7,10,13,16-pentaenoic acid alkyl ester, 0.07 area % or less of (7Z,10Z,13Z,16Z,19Z)-icosa-7,10,13,16,19-pentaenoic acid alkyl ester, and 0.09 area % or less of (4Z,7Z,10Z,13Z,16Z,19Z)-icosa-4,7,10,13,16,19-hexaenoic acid alkyl ester.

4. The method according to claim 1, wherein the raw oil comprises at least 40 area % of eicosapentaenoic acid in the total contained fatty acids.

5. The method according to claim 2, wherein the raw oil comprises at least 40 area % of eicosapentaenoic acid in the total contained fatty acids.

6. The method according to claim 3, wherein the raw oil comprises at least 40 area % of eicosapentaenoic acid in the total contained fatty acids.

* * * * *